United States Patent [19]

Aranyi et al.

[11] Patent Number: 4,513,746
[45] Date of Patent: Apr. 30, 1985

[54] INSTRUMENT FOR APPLYING PLASTIC-LIKE SURGICAL FASTENING DEVICES

[75] Inventors: Ernie Aranyi, Shelton; Richard Ihasz, Milford; Roy D. Gravener, Bethany; Hugh J. Tovey, Westport, all of Conn.

[73] Assignee: United States Surgical Corp., Norwalk, Conn.

[21] Appl. No.: 310,412

[22] Filed: Oct. 9, 1981

[51] Int. Cl.³ .............................................. A61B 17/04
[52] U.S. Cl. .................. 128/334 C; 227/19; 227/156; 227/15
[58] Field of Search .............. 24/221 R; 128/303 A, 128/325, 329, 330, 334 R, 334 C, 337; 227/15–19, 67, 70, 71, 76, 77, 144, 152, DIG. 7, 156; 339/91 R, 128; 402/61, 64, 65, 80 P

[56] References Cited

U.S. PATENT DOCUMENTS

| | | | |
|---|---|---|---|
| 719,475 | 2/1903 | Knight | 227/60 |
| 1,452,373 | 4/1923 | Gomez | 227/18 |
| 2,453,056 | 11/1948 | Zack | 128/334 |
| 2,487,475 | 11/1949 | Powers | 29/243.56 |
| 2,707,783 | 5/1955 | Sullivan | 227/19 X |
| 2,881,762 | 4/1959 | Lowrie | 128/337 |
| 3,069,962 | 12/1962 | Rapata | 85/8.8 |
| 3,093,027 | 6/1963 | Rapata | 85/5 |
| 3,166,072 | 1/1965 | Sullivan, Jr. | 128/346 X |
| 3,252,643 | 5/1966 | Strekopytov et al. | 128/334 R X |
| 3,254,650 | 6/1966 | Collito | 128/334 |
| 3,334,434 | 8/1967 | Melin | 128/330 X |
| 3,357,296 | 12/1967 | Lefever | 411/469 |
| 3,482,428 | 12/1969 | Kapitanov et al. | 72/410 |
| 3,570,497 | 3/1971 | Lemole | 128/335.5 |
| 3,595,201 | 7/1971 | Oudenhoven | 116/114 |
| 3,641,804 | 2/1972 | Oudenhoven | 72/409 |
| 3,744,495 | 7/1973 | Johnson | 128/337 |
| 3,757,389 | 9/1973 | Wiland | 402/1 X |
| 3,795,034 | 3/1974 | Strekopytov et al. | 128/334 R |
| 3,812,859 | 5/1974 | Murphy et al. | 128/330 |
| 3,858,783 | 1/1975 | Kapitanov et al. | 227/108 |
| 4,006,747 | 2/1977 | Kronenthal et al. | 128/335 |
| 4,053,953 | 10/1977 | Flom et al. | 3/13 |
| 4,060,089 | 11/1977 | Noiles | 128/325 |
| 4,122,989 | 10/1978 | Kapitanov et al. | 227/108 |
| 4,147,168 | 4/1979 | Hayes et al. | 128/330 |
| 4,164,224 | 8/1979 | Hastings | 128/330 |
| 4,296,881 | 10/1981 | Lee | 227/30 |

FOREIGN PATENT DOCUMENTS

| | | |
|---|---|---|
| 2830401 | 8/1979 | Fed. Rep. of Germany ... 227/DIG. 1 |
| 2185353 | 4/1974 | France . |
| 2322578 | 4/1977 | France . |
| 392802 | 5/1933 | United Kingdom . |
| 972731 | 10/1964 | United Kingdom . |
| 2023510 | 1/1980 | United Kingdom ............. 128/330 |

*Primary Examiner*—Paul A. Bell
*Attorney, Agent, or Firm*—A. Peter Adler; John E. Nathan; Robert R. Jackson

[57] ABSTRACT

An instrument, method and two-piece plastic-like fastener for surgically fastening tissue by:

(A) placing the tissue between: (1) a retainer of an absorbable material, that is located distally of the tissue and that has a hole which extends longitudinally through it; (2) an elongated rigid piercing member that is located proximally of the tissue, that extends longitudinally, and that has means on its distal end for piercing the tissue; and (3) a fastener of an absorbable material, that is also located proximally of the tissue and that has a distally extending prong which, during distal movement of the fastener, can (a) move distally through an opening pierced in the tissue by the piercing member and (b) then move distally into the retainer hole to hold the retainer and fastener together;

(B) then moving the piercing member distally so that its distal end pierces the tissue; and (C) then moving the fastener distally so that its prong moves through the opening pierced in the tissue and into the retainer hole to hold the retainer and fastener together.

12 Claims, 30 Drawing Figures

STARTING POSITION OF THE ROLLER

TOTAL MOVEMENT OF
THE CAM - 135°
1. 45° - PIERCE TISSUE
2. 45° - RETRACT PIERCER
3. 45° - PIERCER MOVES FORWARD
     WITH PUSHER

FIG. 11

TOTAL MOVEMENT OF
THE CAM - 135°
1. 45° - PIERCE TISSUE
2. 45° - RETRACT PIERCER

FIG. 12

TOTAL MOVEMENT OF
THE CAM - 135°
1. 45° - PIERCE TISSUE
2.    - STAY IN FORWARD
       POSITION 90°

FIG. 13

TOTAL MOVEMENT OF
THE CAM - 135°
1. 45° - PIERCE TISSUE
2. 45° - PARTIAL RETRACT

INSTRUMENT FOR APPLYING PLASTIC-LIKE SURGICAL FASTENING DEVICES

BACKGROUND OF THE INVENTION

This invention relates to an instrument for surgically fastening tissue with plastic-like fastening devices, such as absorbable fastening devices. This invention also relates to a novel two-piece plastic-like fastening device, such as an absorbable fastening device.

Two-piece absorbable fastening devices and means for fastening tissue with such devices have been shown, for example, in U.S. Pat. No. 4,060,089. Such fastening devices have comprised a retainer strip or "retainer" and a fastener strip or "fastener", made in a variety of lengths and sizes from biologically degradable and human-body absorbable materials. The retainer strips has been designed to be held in an elongated rigid anvil which can be placed on one side of the tissue to be fastened, and the fastener strip has been designed to be mounted in alignment with a pusher member located on the other side of the tissue. The fastener strip has been provided with a plurality of barbed prongs which can, when urged through openings pierced in the tissue, fit within holes in the retainer strip to hold the fastener strip and retainer strip securely together.

SUMMARY OF THE INVENTION

In accordance with this invention, an instrument and method are provided for surgically fastening tissue by: (A) placing the tissue between: (1) a retainer that is located distally of the tissue and that has a hole which extends longitudinally through it; (2) an elongated rigid piercing member that is located proximally of the tissue, that extends longitudinally, and that has means on its distal end for piercing the tissue; and (3) a fastener that is also located proximally of the tissue and that has a distally extending prong which, during distal movement of the fastener, can (a) move distally through an opening pierced in the tissue by the piercing member and (b) then move distally into the retainer hole to hold the retainer and fastener together; (B) then moving the piercing member distally so that its distal end pierces the tissue; and (C) then moving the fastener distally so that its prong moves through the opening pierced in the tissue and into the retainer hole to hold the retainer and fastener together. The instrument of this invention comprises:

a first, elongated, longitudinally extending means for moving the piercing member distally with distal movement of the first moving means; the distal end of the first moving means being adapted to move distally to contact, and move distally, the proximal end of the piercing member;

a second, elongated, longitudinally extending means for moving the fastener distally with distal movement of the second moving means; the distal end of the second moving means being adapted to move distally to contact, and move distally, the proximal end of the fastener;

first means, located adjacent to the proximal end of the first moving means, for urging the proximal end of the first moving means to move distally when the proximal end of the first urging means is urged to move distally;

second means, located adjacent to the proximal end of the second moving means, for urging the proximal end of the second moving means to move distally when the proximal end of the second urging means is urged to move distally;

means for simultaneously (1) rotating longitudinally both the first and second urging means so that said urging means become longitudinally aligned with the first and second moving means, respectively, and (2) moving distally both the piercing member and the fastener so that (a) the longitudinal spacing both the piercing member and the tissue, to be fastened, becomes such that the piercing member, when moved distally by the first moving means, can pierce the tissue and (b) the longitudinal spacing between the fastener and the retainer becomes such that the prong of the fastener, when moved distally by the second moving means, can move through the opening pierced in the tissue and into the retainer hole to hold the retainer and fastener together;

a rotatable first cam having a circumferential first cam surface that is progressively closer longitudinally to the retainer and that urges the proximal end of the first urging means to move distally as the first cam undergoes a first rotation; and a rotatable second cam having a circumferential second cam surface that is progressively closer longitudinally to the retainer and that urges the distal end of the second urging means to move distally as the first cam undergoes a further second rotation; the second cam being parallel to the first cam and rotating with the first cam; and the second cam surface not urging the distal end of the second urging means to move distally during the first rotation of the first cam.

Also in accordance with this invention, a two-piece plastic-like fastening device is provided wherein:

the retainer is plastic-like and has a longitudinal extension; the hole in the retainer extends longitudinally through the retainer and its longitudinal extension; and the longitudinal extension of the retainer is laterally expandable about the retainer hole; and the fastener has a laterally extending barb on a lateral surface of its prong; and the fastener is adapted to be moved distally so that the prong and its barb: (1) move distally through an opening pierced in the tissue, to be fastened, and (2) then move distally into the retainer hole, with the barb urging the longitudinal extension of the retainer to expand laterally, until the barb extends distally of the longitudinal extension of the retainer and a proximal surface of the barb engages a laterally extending, distal surface of the longitudinal extension of the retainer about the retainer hole.

BRIEF DESCRIPTION OF THE DRAWINGS

FIG. 1 is a perspective view of one embodiment of an instrument for applying two-piece absorbable surgical fastening devices in accordance with this invention. FIG. 1 shows an anvil assembly on a U-shaped member on the distal end of the housing of the instrument. The anvil assembly is located distally of a fastener-carrying assembly on the distal end of a longitudinally movable, support member which extends from the distal end of the housing. Tissue, to be fastened, can be inserted between the anvil and fastener-carrying assemblies.

FIG. 2 is a fragmentary perspective view of the proximal portions of the instrument of FIG. 1. Proximal portions of the housing of the instrument have been removed to show a mechanism that can be used, when the handles of the instrument are squeezed together, to actuate means for: (a) distally moving piercing members in the fastener-carrying assembly so that they pierce the tissue that is to be fastened; and (b) then distally moving fasteners in the fastener-carrying assembly so that distally extending prongs on the fasteners move distally through openings pierced in the tissue and then into holes in retainers in the anvil assembly to hold the fasteners and retainers together and thereby fasten the tissue.

FIG. 4 shows portions of the actuating mechanism that are associated with, and located distally of, its first rotatable cam. In FIG. 4, the elements of the actuating mechanism are arranged as they are when the anvil assembly and fastener-carrying assembly are spaced longitudinally apart, as in FIGS. 1 and 14, so that tissue, to be fastened, can be inserted between them. As the actuating mechanism is shown in FIG. 4, it cannot be used, when the handles of the instrument are squeezed together, to cause distal movement of the piercing members and fasteners.

FIG. 6 shows portions of the actuating mechanism associated with, and located distally of, its first rotatable cam. In FIG. 6, the elements of the actuating mechanism are arranged as they are when the longitudinal space between the anvil and fastener-carrying assemblies is as shown in FIG. 15 so that the actuating mechanism can be used to cause the piercing members to be moved distally and then cause the fasteners to be moved distally. As the actuating mechanism is shown in FIG. 6, it has been used, by partially squeezing the handles of the instrument together, to cause the first cam to rotate and cause thereby the piercing members to be moved distally.

FIG. 8 shows portions of the actuating mechanism associated with, and located distally of, its second rotatable cam. In FIG. 8, the elements of the actuating mechanism are arranged as they are after the actuating mechanism has been used, by fully squeezing the handles of the instrument together, to cause the second cam to rotate and cause thereby the fasteners to be moved distally.

FIGS. 19 and 21 are side views, FIG. 20 is a top view taken along line 20—20 in FIG. 19, and FIG. 22 is a top view taken along line 22—22 in FIG. 21. FIGS. 19 to 22 show the piercing and subsequent fastening of tissue by the anvil and fastener-carrying assemblies and their two parallel rows of retainers, fasteners and piercing members.

DETAILED DESCRIPTION OF THE PREFERRED EMBODIMENT

Although the principles of this invention are applicable to other surgical fastening instruments, the invention will be fully understood from an explanation of its application to a preferred embodiment of an instrument for fastening two portions of tissue together with two-piece plastic-like surgical fastening devices as shown in FIGS. 1 to 30.

Figures 1, 2:
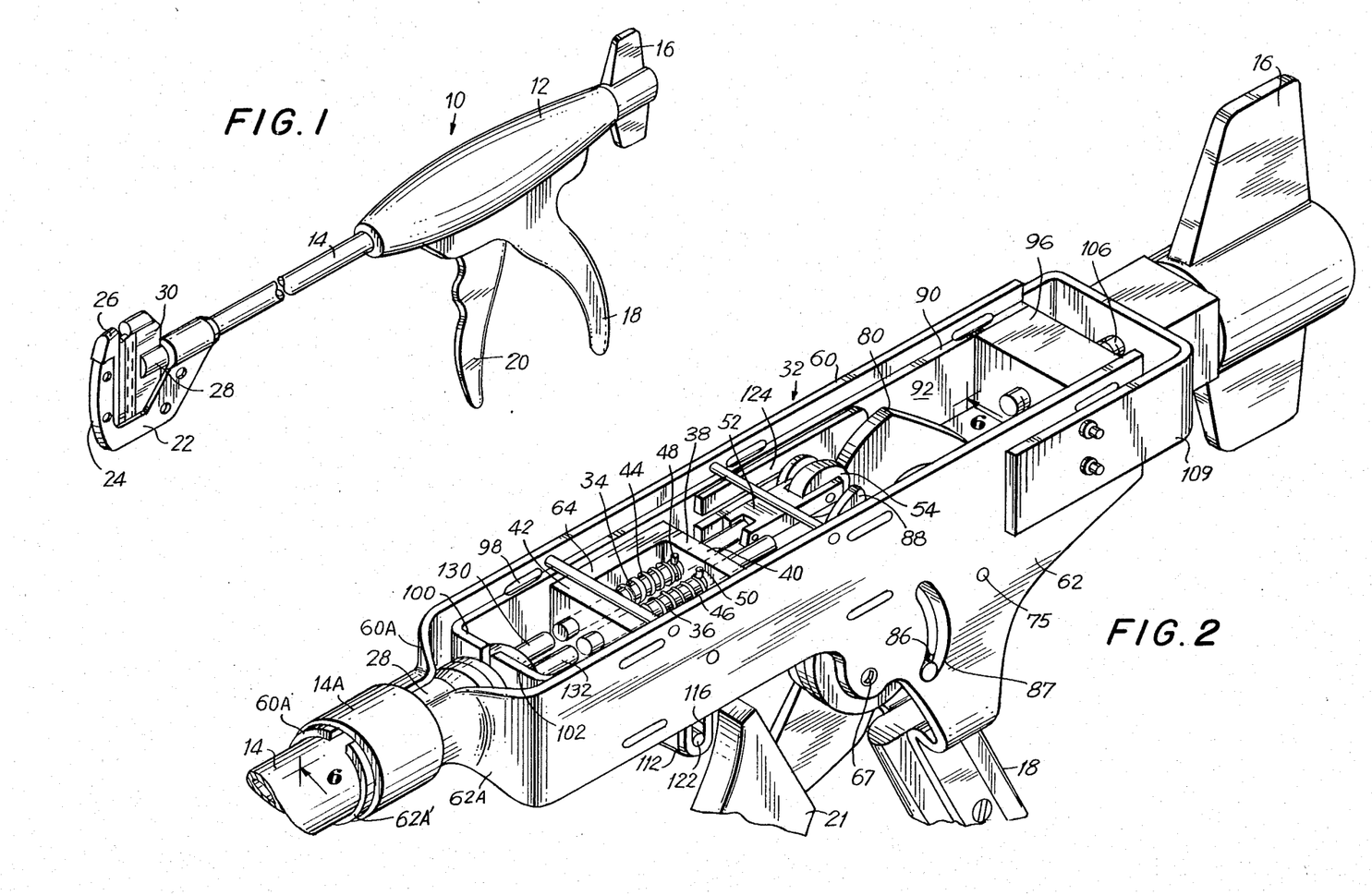

Shown in FIG. 1 is an instrument, generally 10, for applying two-piece absorbable fastening devices in accordance with this invention. The instrument 10 includes an elongated rigid body or housing 12, having a longitudinally extending, tubular portion 14 on its distal end. On the proximal end of the housing 12 is a rotatable wing nut 16. Beneath the housing 12 are a pair of rigid handles 18 and 20. One handle 18 is fixed on the instrument 10, while the second handle 20 is pivotally connected to the instrument. The lower portions 21 of the second handle 20, beneath the second handle's pivotal connection to the instrument 10, can be moved proximally toward the fixed first handle 18, e.g., by squeezing the lower portions of the handles 18 and 20 together.

Figure 14:
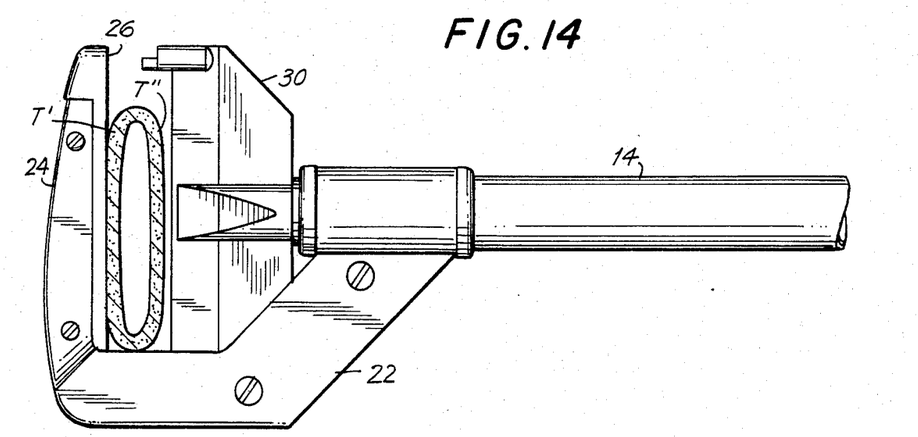
FIGS. 14 and 15 are fragmentary side views of the distal portions of the instrument of FIG. 1. Shown are the anvil and fastener-carrying assemblies positioned about tissue that is to be fastened between them.
Figure 15:
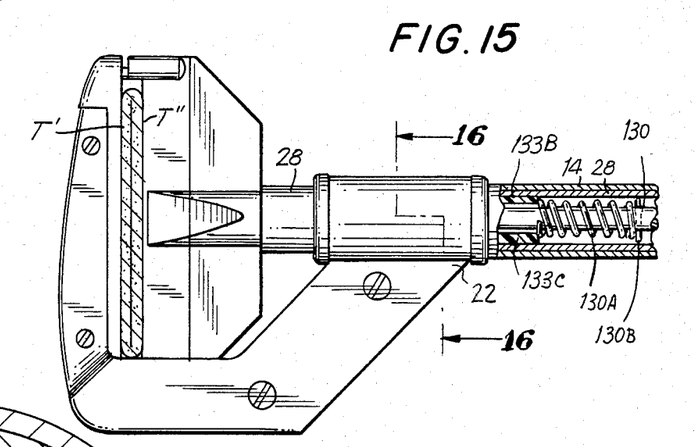

As shown in FIGS. 1, 14 and 15, a rigid, longitudinally extending, U-shaped member 22 is mounted on the distal end of the tubular housing portion 14 of the instrument 10. On the proximal side of the distal leg 24 of the U-shaped member 22 is provided an anvil assembly, generally 26, of this invention which will be described below. The anvil assembly 26 contains two parallel rows of absorbable one-piece retainers, generally 26A, which will also be described below. If desired, the anvil assembly 26 can be detachably connected in a conventional manner to the proximal side of the distal leg 24 of the U-shaped member 22 so that the anvil assembly can be replaced after use.

As also shown in FIGS. 1, 14 and 15, a longitudinally movable, rigid, tubular support member 28 is provided within the tubular housing portion 14 of the instrument 10. The support member 28 extends distally outward of the tubular housing portion 14. A fastener-carrying assembly, generally 30, which will be described below, is provided on the distal end of the support member 28. The fastener-carrying assembly 30 contains two parallel rows of rigid, preferably metal (e.g., stainless steel), piercing members, generally 30A, and two parallel rows of absorbable one-piece fasteners, generally 30B, which will be described below. If desired, the fastener-carrying assembly 30 can be detachably connected in a conventional manner to the distal end of the support member 28 so that the fastener-carrying assembly can be replaced after use.

Figure 3:
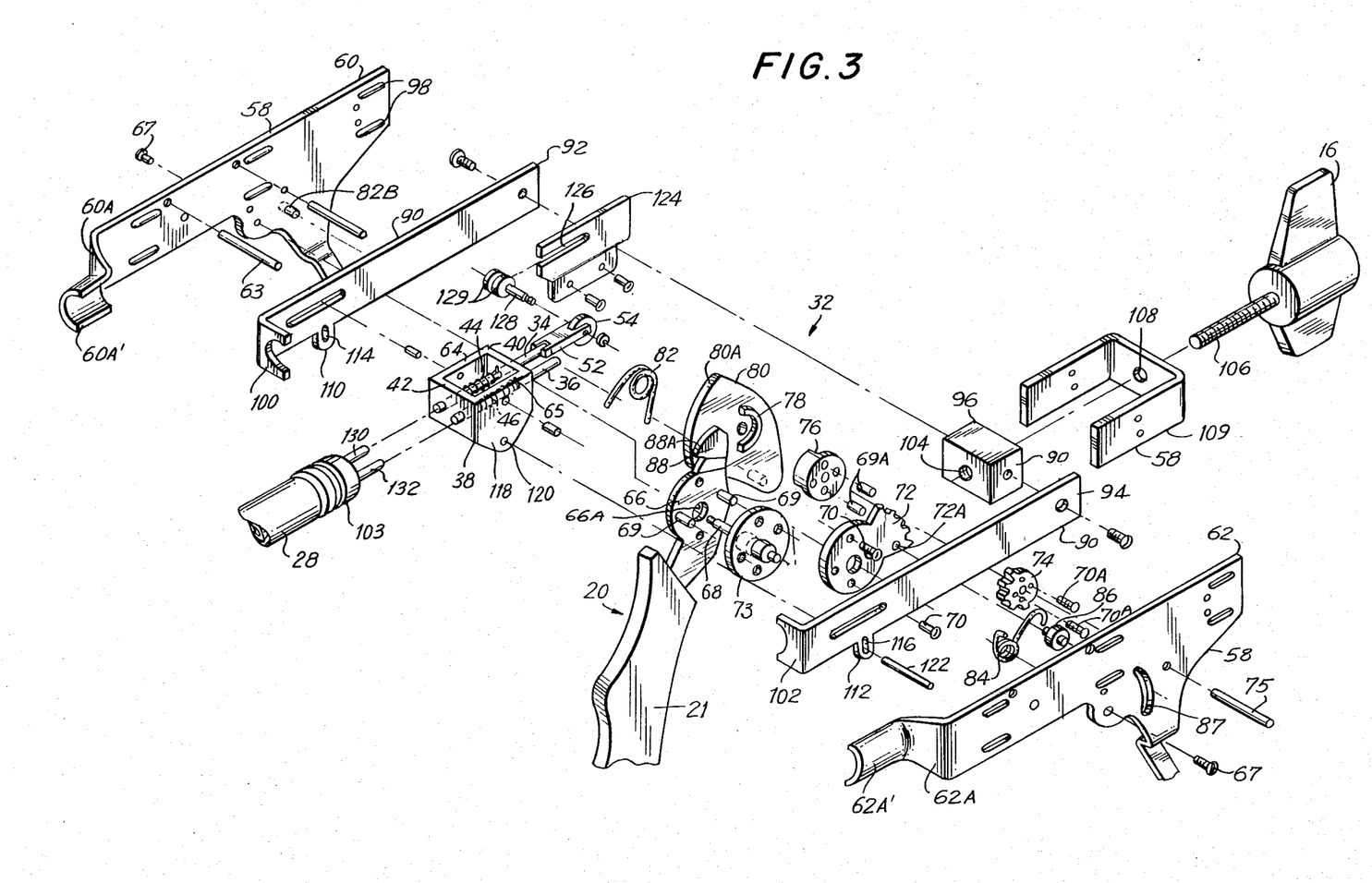
FIG. 3 is an exploded perspective view of the actuating mechanism of the instrument shown in FIG. 2.

Shown in FIGS. 2 and 3 is a mechanism, generally 32, that can be used, when the lower portion 21 of the second handle 20 is moved proximally toward the fixed first handle 18, for actuating means in the instrument 10 for: (a) piercing the tissue, to be fastened, with the piercing members 30A in the fastener-carrying assembly 30; and (b) then urging the fasteners 30B in the fastener-carrying assembly 30 into openings pierced in the tissue and then into holes in the retainers 26A in the anvil assembly 26.

The actuating mechanism 32 is located in the proximal portions of the housing 12 of the instrument 10. The mechanism 32 comprises a pair of parallel rigid elongated pusher rods 34 and 36. The pusher rods 34 and 36 are located in a rigid rectangular frame 38. The pusher rods 34 and 36 extend slidably through separate holes in two, laterally extending, opposite sides 40 and 42 of the rectangular frame 38. Provided about each pusher rod 34 and 36, within the rectangular frame 38, is a spring 44 and 46. The distal end of each spring 44 and 46 is adjacent to the distal, laterally extending side 42 of the rectangular frame 38. The proximal end of each spring 44 and 46 is adjacent to a pin 48 and 50, extending laterally outward of each pusher rod 34 and 36, so that the springs 44 and 46 are adapted to urge the pusher rods 34 and 36 and their pins 48 and 50 to move proximally.

In the actuating mechanism 32 of the instrument 10, the proximal end of a first pusher rod 34 is pivotally connected to the distal end of a rigid, longitudinally extending, connecting member 52. The proximal end of the connecting member 52 is pivotally connected to a rotatable cam follower 54.

Surrounding and supporting the actuating mechanism 32 of the instrument 10 is a rigid frame, generally 58, within the proximal portions of the housing 12. The frame 58 includes two, elongated, longitudinally extending, lateral side members 60 and 62. The ends of a first rigid, laterally extending shaft 63 are connected to the two lateral side frame members 60 and 62. The other two opposite sides 64 and 65 of the rectangular frame 38 are rotatably mounted on the first shaft 63 so that the rectangular frame 38 is rotatably connected to the two lateral side frame members 60 and 62.

As shown in FIGS. 2 and 3, the distal ends of the two lateral side frame members 60 and 62 are provided with bifurcated extensions 60A and 62A, respectively, which extend laterally towards each other. The lateral side frame member extensions 60A and 62A have arcuate ends with distally extending, arcuate projections 60A' and 62A', respectively. The arcuate projections 60A' and 62A' are held on laterally opposite sides of the proximal end of the tubular housing portion 14 by a circular band 14A about the arcuate projections 60A' and 62A' and the proximal end of the tubular housing portion 14.

Figures 6, 7:
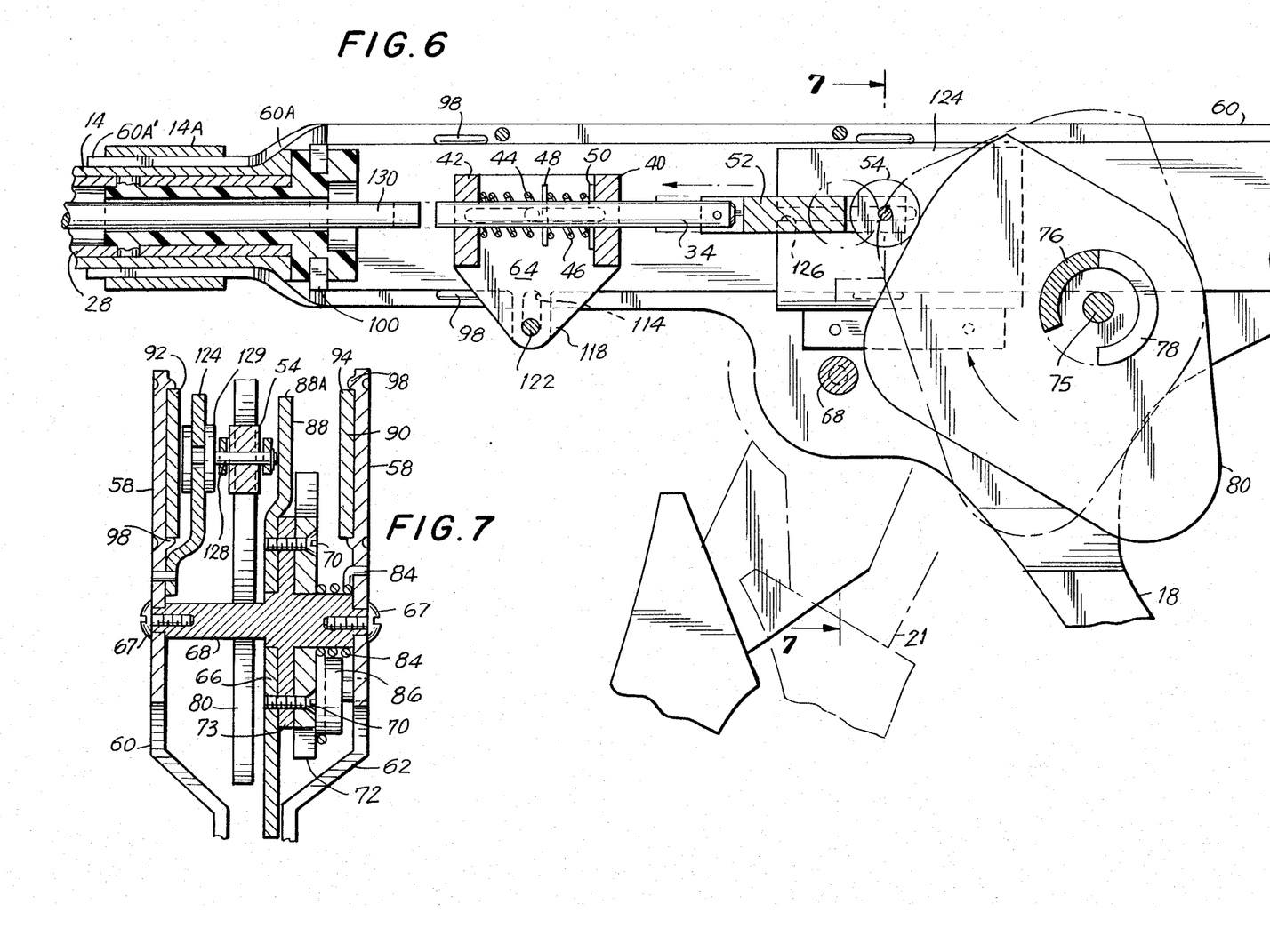
FIG. 6 is a fragmentary sectional view, similar to FIG. 4.
FIG. 7 is a sectional view taken along line 7—7 in FIG. 6.

As seen from FIGS. 3 and 7, the upper portions 66 of the movable second handle 20 are also rotatably connected to the two lateral side frame members 60 and 62 by means of a pair of laterally extending screws 67 and a second rigid, laterally extending shaft 68. The screws 67 are threaded into laterally opposite ends of the second shaft 68, and the shaft 68 extends laterally through a laterally extending hole 66A in the upper second handle portions 66. The second shaft 68 is rotatably mounted in holes in the first and second, lateral side frame members 60 and 62, respectively. The upper second handle portions 66, about the hole 66A, are also connected by two, laterally extending, dowel pins 69 and two laterally extending screws 70 to a segmented drive gear 72. The drive gear 72 is also rotatably mounted about the second shaft 68 so that: (a) it is rotatably connected to the lateral side frame members 60 and 62 and (b) it rotates with the upper portions 66 of the second handle 20 about the second shaft 68. A circular spacer 73, integral with the second shaft 68, is preferably provided between the upper second handle portions 66 and the drive gear 72, and the dowel pins 69 and screws 70, connecting the upper second handle portions 66 and the drive gear 72, preferably extend through the spacer 73.

Figures 4, 5:
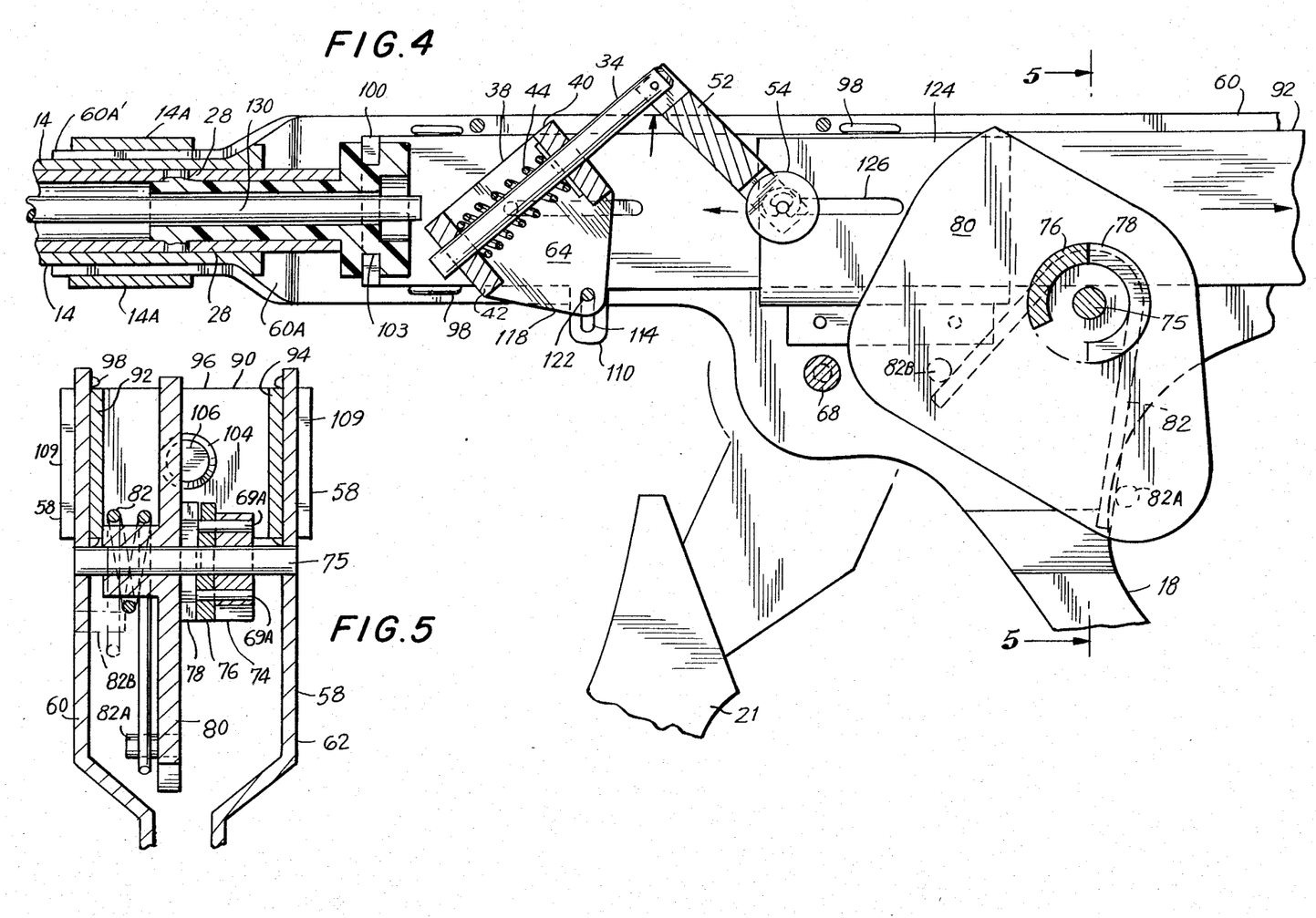
FIG. 4 is a fragmentary sectional view taken along the longitudinal center line of the instrument.
FIG. 5 is a sectional view taken along line 5—5 in FIG. 4.
Figures 8, 9:
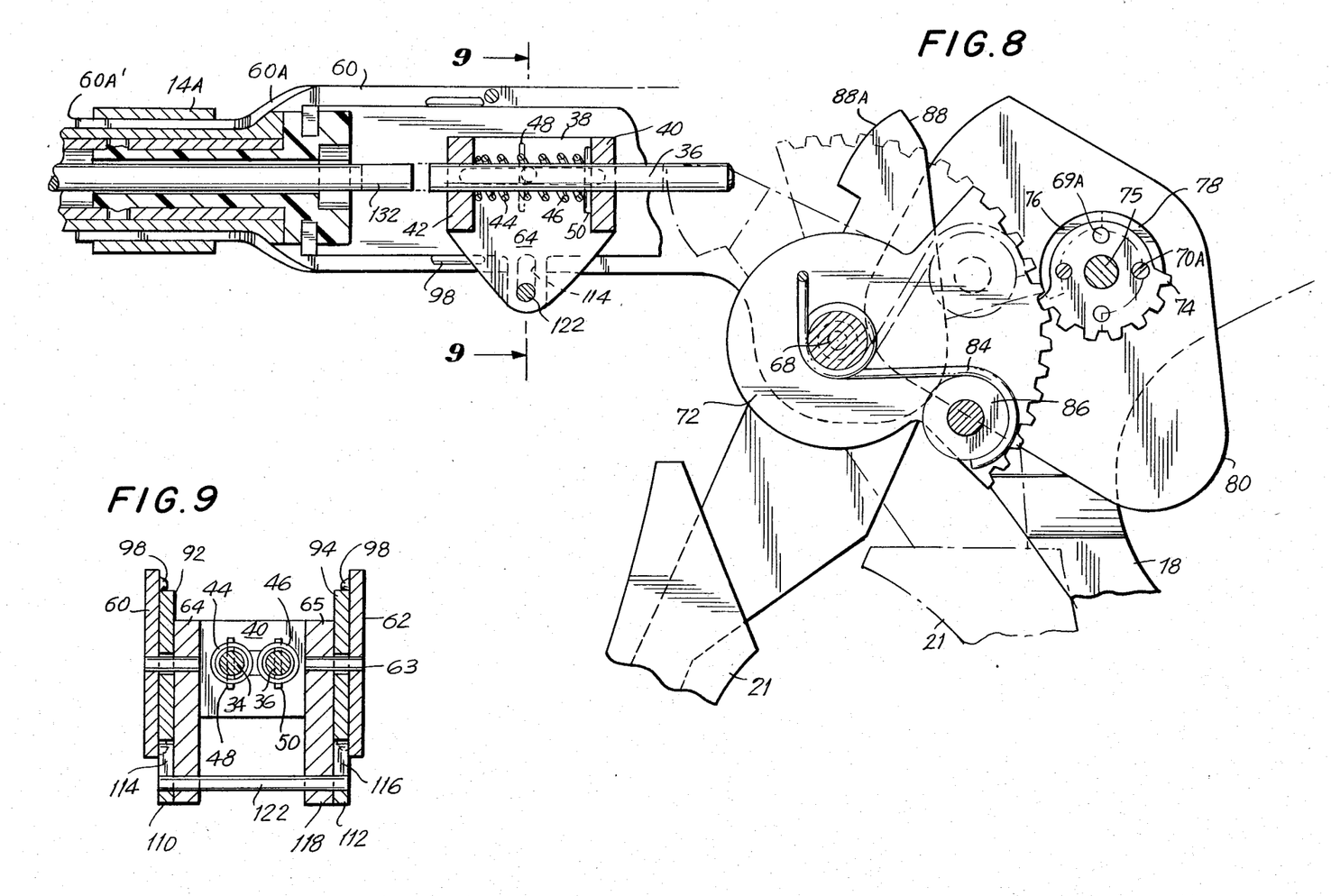
FIG. 8 is a fragmentary sectional view, similar to FIG. 6.
FIG. 9 is a sectional view taken along line 9—9 in FIG. 8.
Figure 10:
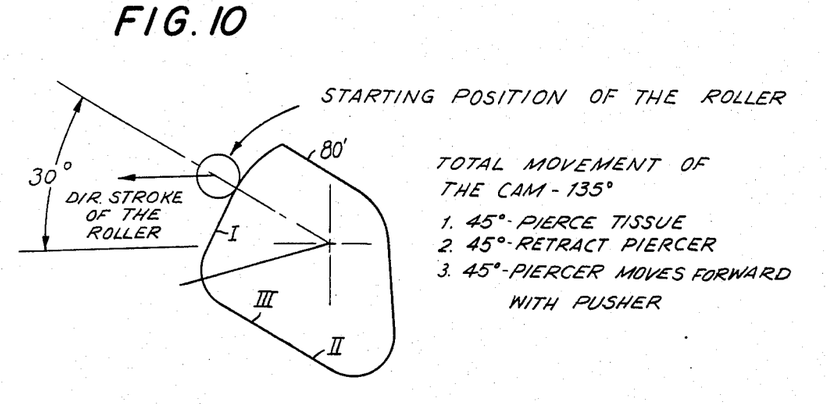
FIGS. 10 to 13 are side views of different embodiments of the first cam of the actuating mechanism. Rotation of the first cam regulates the longitudinal movement of the piercing members, used to pierce openings in the tissue, to be fastened.
Figure 11:
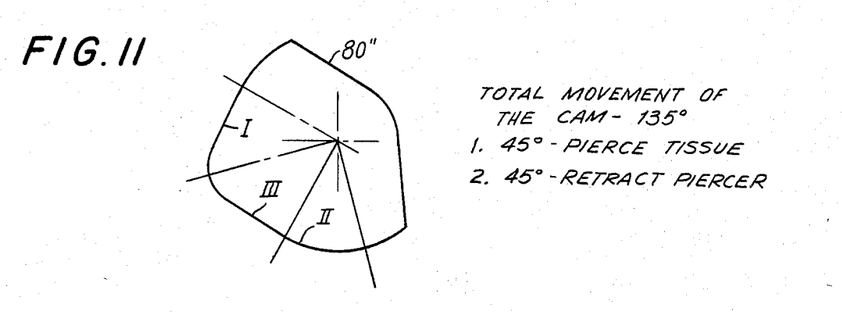

As shown in FIGS. 3, 5 and 8, the drive gear 72 is coupled to a longitudinally adjacent, segmented driven pinion gear 74. The driven gear 74 is also rotatably connected to the lateral side frame members 60 and 62 by a third rigid, laterally extending shaft 75, extending through the driven gear 74. The driven gear 74 is connected by two, laterally extending, dowel pins 69A and two, laterally extending screws 70A, to a laterally adjacent, drive clutch 76, rotatably mounted on the third shaft 75. It is preferred that the drive clutch 76 extend much less than 180° about the third shaft 75, preferably approximately 112.5° about the third shaft 75. The drive clutch 76 is coupled to a longitudinally adjacent, driven clutch 78, which preferably extends approximately 180° about the third shaft 75. The driven clutch 78 is mounted on one lateral side of a first cam 80 that is laterally adjacent to the drive clutch 76. The first cam 80 and the driven clutch 78 are also rotatably mounted on the third shaft 75. Thereby, the drive gear 72, driven gear 74, drive clutch 76, driven clutch 78 and first cam 80 are adapted to rotate longitudinally with longitudinal rotation of the upper second handle portions 66 about the second shaft 68 upon proximal movement of the lower portions 21 of the second handle 20.

As also shown in FIGS. 3 and 5, a third spring 82 is located on the other lateral side of the first cam 80 about the third shaft 75. The ends of the third spring 82 are longitudinally biased against a projection 82A on the lower portions of the first cam 80 and a projection 82B on the adjacent first lateral side member 60 of the frame 58. The projections 82A and 82B extend laterally towards each other. The third spring 82 resists longitudinal rotation of the first cam 80 which would result in distal movement of the projection 82A on the first cam 80.

As seen from FIGS. 3, 7 and 8, a longitudinally extending, fourth spring 84 is connected, at its proximal end, to a laterally extending, rigid pin 86 within the frame 58. One end of the pin 86 is located in a hole 72A in the lateral surface of the proximal lower end of the drive gear 72, adjacent to its gear teeth. The other end of the pin 86 is slidably located in an arcuate slot 87 in the second lateral side member 62 of the frame 58. The distal end of the fourth spring 84 is wrapped about the first screw 67 and the second shaft 68 and is connected to the second lateral side frame member 62. The proximal end of the fourth spring 84 is wrapped about the pin 86. Thereby, the fourth spring 84 serves to resist longitudinal rotation of the drive gear 72 and pin 86.

Mounted on top of the upper portions 66 of the movable second handle 20 is an upwardly extending finger or second cam 88. The second cam 88 is adapted to rotate longitudinally and move distally with longitudinal rotation of the upper second handle portions 66 about the second shaft 68 when the lower portions 21 of the second handle 20 are moved proximally.

In the actuating mechanism 32 of the instrument 10, the first cam 80 has a circumferential first cam surface 80A. The first cam surface 80A is located proximally of the circumferential surface of the cam follower 54, the connecting member 52 and the first pusher rod 34 in the rectangular frame 38 as shown in FIGS. 4 and 6. The second cam 88 has a distally extending, circumferential second cam surface 88A. As shown in FIG. 8, the second cam surface 88A is located proximally of the second pusher rod 36 in the rectangular frame 38.

Provided within the frame 58 is a bifurcated pusher bar 90 as shown in FIGS. 2 and 3. The pusher bar 90 comprises two rigid, elongated, longitudinally extending, lateral side members 92 and 94, connected by a rigid rectangular block 96 at their proximal ends. Each lateral side pusher member 92 and 94 is located adjacent to one of the facing surfaces of the lateral side frame members 60 and 62 and is adapted to slide along the facing surface of its adjacent lateral side frame member 60 and 62. Preferably, two parallel, longitudinally extending sets of guides 98 project laterally from the upper and lower portions of the facing surfaces of the two lateral side frame members 60 and 62. The upper and lower sets of guides 98 serve to keep the lateral side pusher members 92 and 94 moving longitudinally along the lateral side frame members 60 and 62 between the sets of guides 98.

As shown in FIGS. 2 and 3, the distal ends of the lateral side pusher members 92 and 94 are provided with bifurcated extensions 100 and 102, respectively, which extend laterally towards each other. The bifurcated pusher extensions 100 and 102 have arcuate ends which are located in an annular groove 103 in the outer surface of the support member 28. Thereby, the bifurcated pusher extensions 100 and 102 hold between them laterally opposite sides of the proximal end of the support member 28.

In the actuating mechanism 32, a longitudinally extending, threaded hole 104 is provided through the block 96 of the pusher bar 90. A longitudinally extending threaded rod 106 is provided on the distal end of the wing nut 16. The threaded rod 106 extends through a hole 108 in a proximal member 109 of the frame 58 and is threadedly engaged with the hole 104 in the pusher block 96.

The lower edge of each lateral side pusher member 92 and 94 of the pusher bar 90 is provided with a downwardly extending projection 110 and 112. Each projection 110 and 112 has a downwardly extending, elongated slot 114 and 116 extending laterally through it. Positioned between the projections 110 and 112 of the lateral side pusher members 92 and 94 are the lower portions 118 of the other two opposite sides 64 and 65 of the rectangular frame 38 which contains the pusher rods 34 and 36. Provided in the lower portions 118 of each of the other two opposite sides 64 and 65 of the rectangular frame 38 is a hole 120. The slots 114 and 116 in the projections 110 and 112 of the lateral side pusher members 92 and 94 and the holes 120 in the lower portions 118 of the other two opposite sides 64 and 65 of the rectangular frame 38 are pivotally connected by a fourth rigid, laterally extending shaft 122 extending through all these holes 120 and slots 114 and 116.

Mounted in the frame 58 on the first lateral side frame member 60 is a bracket 124 having a slot 126 extending longitudinally from the distal end of the bracket 124. Slidably located in the slot 126 is one end of a laterally extending, fifth rigid shaft 128. Two, laterally spaced, annular guides 129 are provided on the one end of the fifth shaft 128 to hold the one end of the fifth shaft 128 in the slot 126 of the bracket 124 between the guides 129. The other end of the fifth shaft 128 has a snap ring which fits into a hole at the center of the cam follower 54 so as to support the cam follower 54 and allow it to rotate about the fifth shaft 128.

Located distally of the actuating mechanism 32 of the instrument 10, as described above, is a first rigid elongated rod 130 and a second rigid elongated rod 132. The first and second elongated rods 130 and 132 extend longitudinally through the support member 28 which extends through the tubular housing portion 14. As seen from FIGS. 2, 4, 6 and 8, when the pusher rods 34 and 36 extend longitudinally, the proximal ends of the first and second elongated rods 130 and 132 are adjacent to the distal ends of the first and second pusher rods 34 and 36, respectively.

Figure 16:
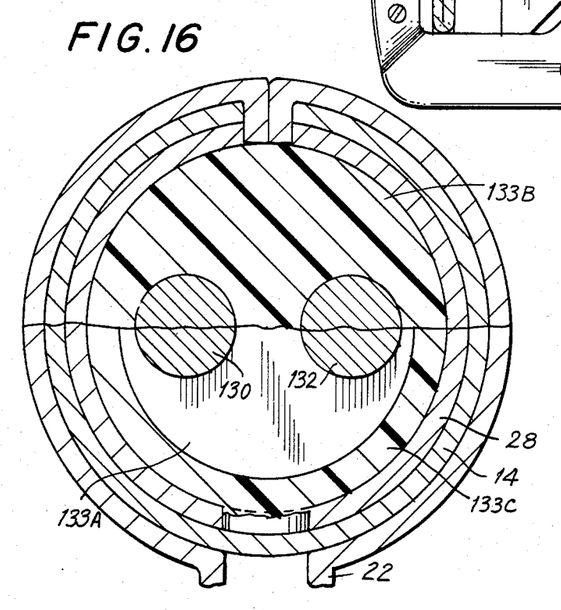
FIG. 16 is a sectional view taken along line 16—16 in FIG. 15.

As shown in FIG. 16, a rigid annular spacer 133 is mounted in the distal end of the support member 28. The central portions 133A of the spacer 133 fit closely about the elongated rods 130 and 132 at about the longitudinal center of the space 133, near the distal end of the support member 28. The upper and lower portions 133B and 133C, respectively, of the spacer 133 extend proximally of its central portions 133A within the support member 28. The spacer 133 is adapted to: (a) align the elongated rods 130 and 132 in the support member 28 as shown in FIG. 16 and (b) permit the elongated rods 130 and 132 to move smoothly within the support member 28 in a longitudinal direction.

As shown in FIG. 15, a fifth spring 130A is also provided about the first elongated rod 130. The fifth spring 130A is located between: (a) the proximal ends of the upper and lower portions 133B and 133C of the spacer 133 and (b) a pin 130B extending laterally outward of the first elongated rod 130. The fifth spring 130A is adapted to urge the pin 130B and the first elongated rod 130 to move proximally when the first elongated rod 130 has been moved distally, relative to the support member 28, from the first elongated rod's position in FIG. 15 and the spring 130A has been longitudinally compressed by the pin 130B.

As seen from FIGS. 19 to 22, the distal ends of the first and second elongated rods 130 and 132 extend into the fastener-carrying assembly 30 and are provided with projections 134 and 136, respectively, which extend laterally towards each other. The first projection 134 on the first elongated rod 130 extends through a close fitting slot 138 in the proximal end of a longitudinally extending, elongated, rigid, piercing member driver 140 in the fastener-carrying assembly 30. The second projection 136 on the second elongated rod 132 extends through a close fitting slot 142 in the proximal end of a longitudinally extending, rigid, elongated, bifurcated fastener driver 144 in the fastener-carrying assembly 30.

Figure 17:
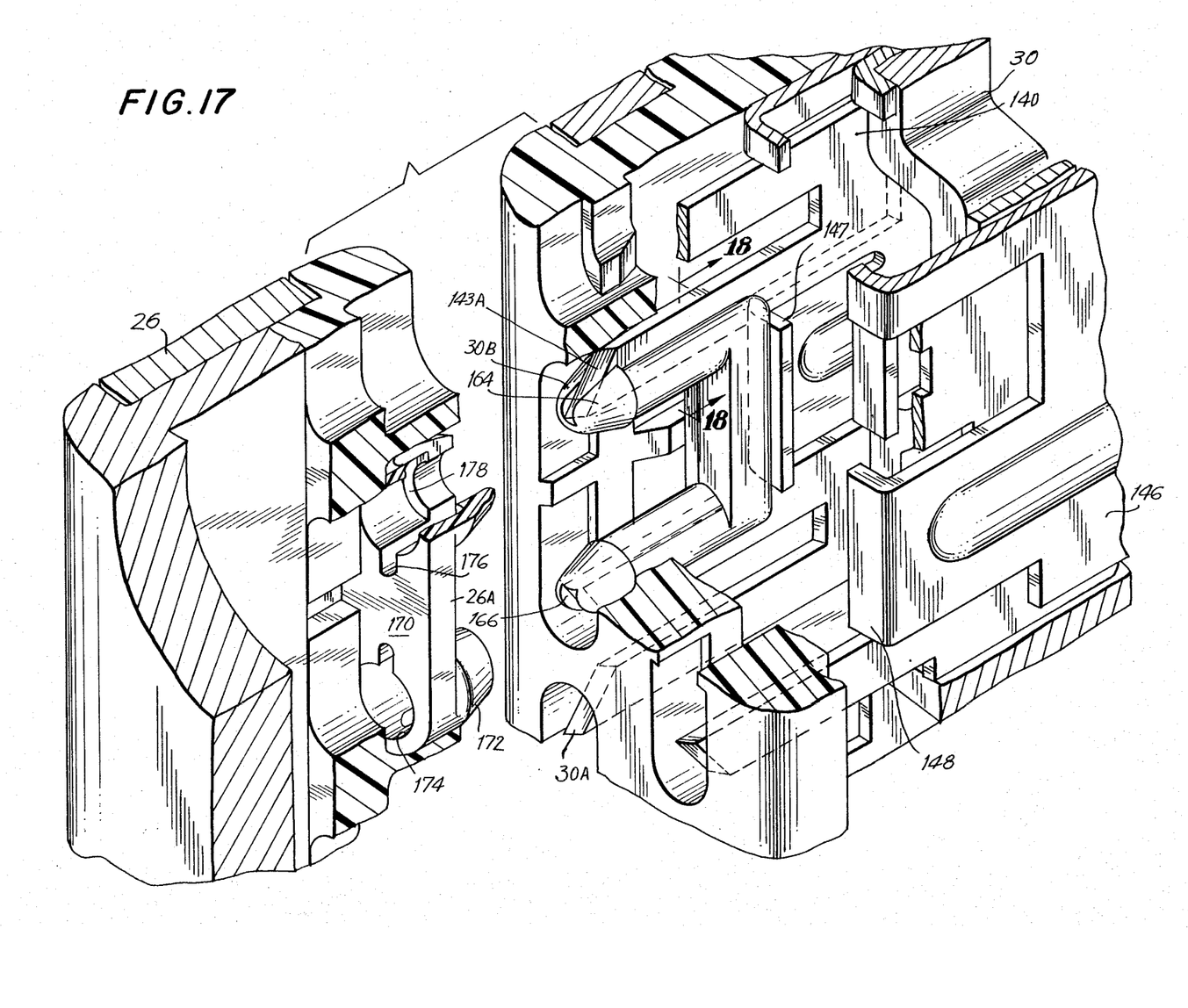
FIG. 17 is a cut-away perspective view of portions of the anvil assembly and its retainers and portions of the fastener-carrying assembly and its piercing members and fasteners.
Figure 18:
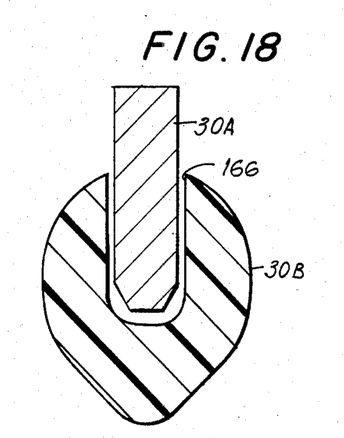
FIG. 18 is a sectional view taken along lines 18—18 in FIG. 17.
Figure 19:
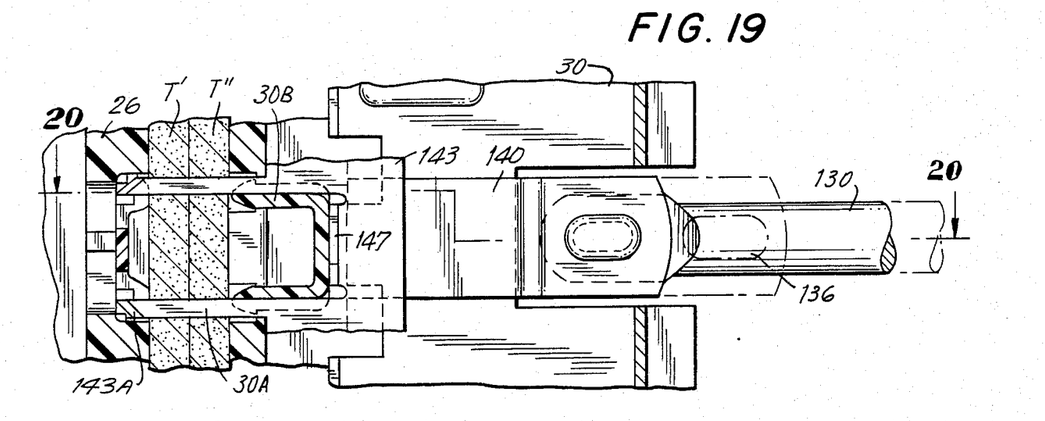
FIGS. 19 to 22 are partial sectional views of the proximal portions of the instrument of FIG. 1.

The distal end of the piercing member driver 140 is connected to two parallel, laterally extending rows 143 of longitudinally extending, piercing members 30A in the fastener-carrying assembly 30. The piercing members 30A are rigid, elongated members, the distal ends 143A of which are adapted to pierce tissue when urged distally against the tissue. Preferably, the distal ends 143A of the piercing members 30A are beveled knife blades as shown in FIG. 17.

The fastener driver 144 comprises two longitudinally extending, parallel, fastener driver members 145 and 146, located on laterally opposite sides of the piercing member driver 140 in the fastener-carrying assembly 30. The distal ends of the fastener driver members 145 and 146 are provided with forked extensions 147 and 148, respectively, which extend laterally towards each other. Two parallel rows of fasteners 30B extend distally from the fastener driver members 145 and 146 and their forked extensions 147 and 148. The distal surfaces of the fastener driver extensions 147 and 148 are adapted to abut against, and urge distally, the fasteners 30B when the fastener driver 144 is urged distally.

Located distally of the fastener-carrying assembly 30 is the anvil assembly 26, located on the proximal side of the distal end 24 of the U-shaped member 22. As shown in FIG. 17, the anvil assembly 26 serves to frictionally hold two parallel rows of retainers 26A where they can be used to fasten tissue with the fasteners 30B. The anvil assembly 26 also serves to prevent the tissue, being fastened, from moving distally and to prevent the retainers 26A from moving either laterally or distally while the fasteners 30B are being urged distally against the tissue and the retainers 26A to fasten the fasteners and retainers 30B and 26A together about the tissue. In this regard, the anvil assembly 26 holds the retainers 26A distally of tissue positioned between the anvil and fastener-carrying assemblies 26 and 30.

In accordance with this invention, the instrument 10 can be used to surgically fasten tissue with a plurality of retainers 26A, made of an absorbable material, and a plurality of fasteners 30B, made of an absorbable material.

Figure 23:
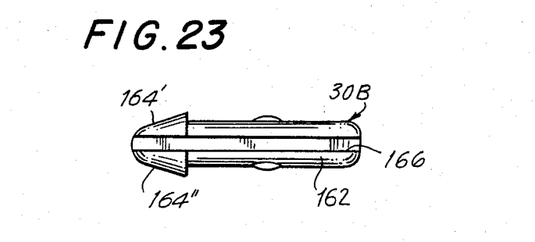
FIG. 23 is a top view of one embodiment of an absorbable surgical fastener of this invention as shown in FIGS. 20 and 22.
Figure 24:
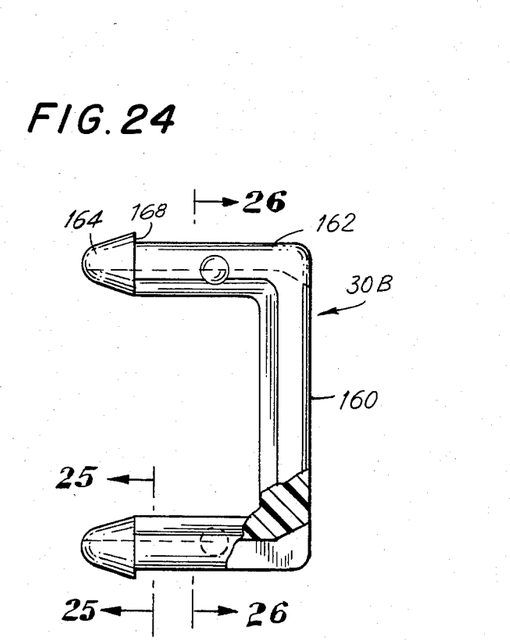
FIG. 24 is a partial sectional side view of the fastener shown in FIG. 23.
Figure 25:
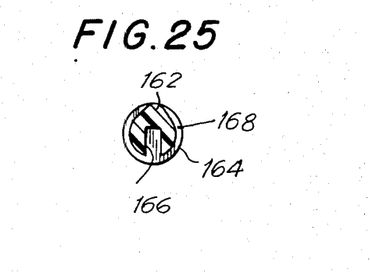
FIG. 25 is a sectional view taken along line 25—25 in FIG. 24.
Figure 26:
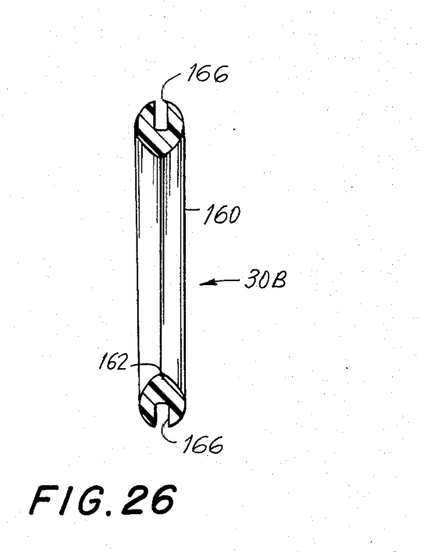
FIG. 26 is a sectional view taken along line 26—26 in FIG. 24.
Figure 27:
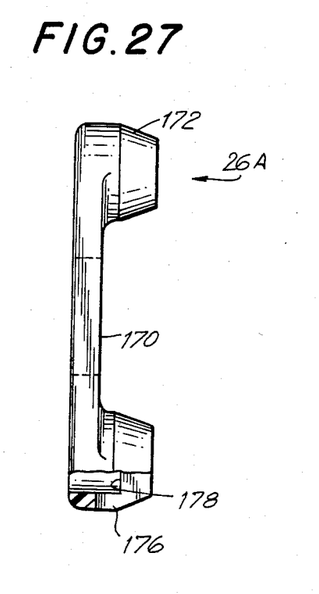
FIG. 27 is a partial sectional side view of one embodiment of a retainer of this invention as shown in FIGS. 19 and 21.
Figure 28:
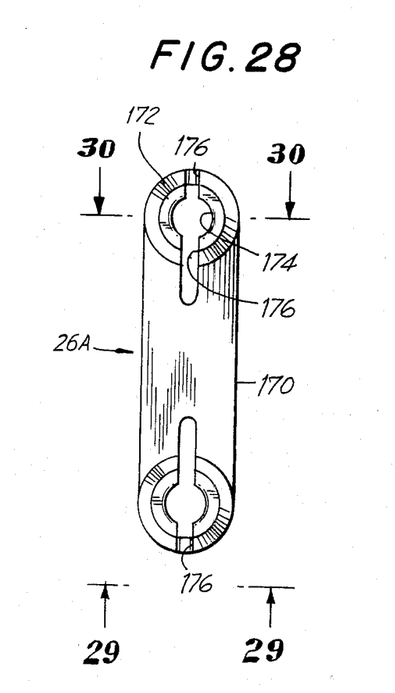
FIG. 28 is another side view of the retainer shown in FIG. 27.
Figure 29:
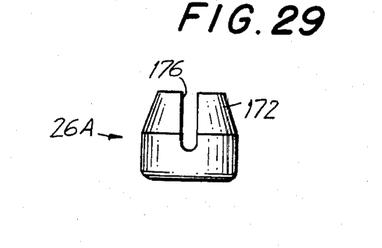
FIG. 29 is a top view of the retainer of FIG. 28, taken along line 29—29 in FIG. 28.
Figure 30:
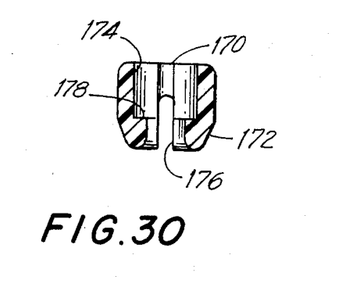
FIG. 30 is a sectional view taken along line 30—30 in FIG. 28.

As shown in FIGS. 23 to 26, each fastener 30B of this invention preferably comprises a laterally extending base 160 having one or more, distally extending, parallel prongs 162. The base 160 of the fastener 30A is adapted to be urged to move distally by one of the fastener driver extensions 147 and 148. Preferably, the fastener 30B has two prongs 162 on laterally opposite ends of its base 160. Provided on a lateral surface of each prong 162 is one or more, laterally extending barbs 164. Preferably, a distal surface of a barb 164 on each prong 162 comprises a distal surface of the prong itself. In each prong 162 and its proximally located portions of the base 160 is a longitudinally extending channel 166, through which a piercing member 30A can move longitudinally through the fastener 30B. It is preferred that each fastener channel 166 extend laterally outward of a prong 162 and that a pair of barbs 164' and 164" be provided on the prong on laterally opposite sides of the fastener channel 166 as shown in FIG. 23. It is also preferred that each barb 164 have a sharply delineated proximal surface 168. In this regard, it is preferred that the proximal surface 168 of the barb 164 form an angle of no more than about 90° with the proximally located portions of the lateral surface of the prong 162 on which the barb 164 is located. It is also preferred that the proximal barb surface 168 extend around the entire circumference of the proximally located portions of the lateral surface of the prong 162. It is further preferred that the lateral cross-section of each prong 162 be generally annular as shown in FIG. 25 and the longitudinal cross-section of each barb be tapered as seen from FIG. 23.

As shown in FIGS. 27 to 30, each retainer 26A of this invention preferably comprises a laterally extending base 170 having one or more, longitudinal, preferably proximal, extensions 172. The base 170 of the retainer 26A is adapted to be frictionally held in the anvil assembly 26. Preferably, the retainer 26A has two parallel longitudinal extensions 172 on laterally opposite ends of its base 170. In each longitudinal extension 172 and its longitudinally located portions of the base 170 is a longitudinally extending hole 174. Each longitudinal extension 172 also includes at least one longitudinal slit 176, communicating with its retainer hole 174 and a lateral surface of the longitudinal extension 172. Preferably, each longitudinal extension 172 includes two longitudinal slits 176 on laterally opposite sides of the longitudinal extension 172. The longitudinal slits 176 make each longitudinal extension 172 of the retainer 26A laterally expandable about the retainer hole 174 in the longitudinal extension 172. At the distal end of each laterally expandable, longitudinal extension 172, an internal, laterally extending, distal surface 178 is also preferably provided about the retainer hole 174. In this regard, the distal surface 178 preferably extends around the entire circumference of the retainer hole 174. Preferably, the lateral cross-section of each longitudinal extension 172 of a retainer and each retainer hole 174 is annular as seen from FIG. 28.

Figure 20:
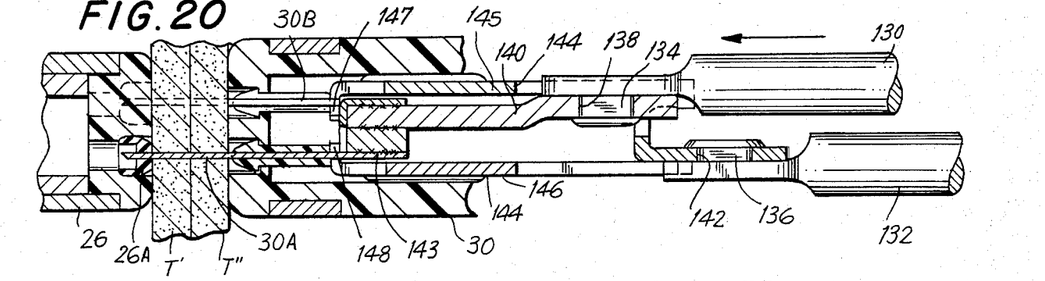
Figure 21:
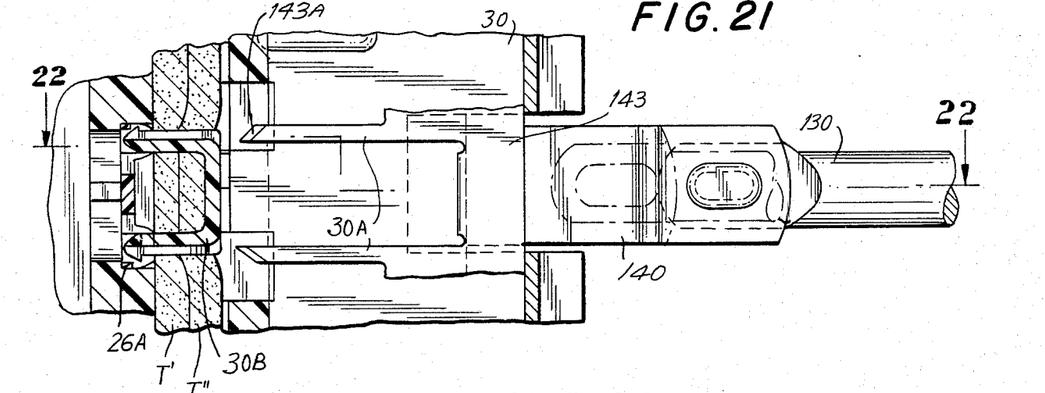
Figure 22:
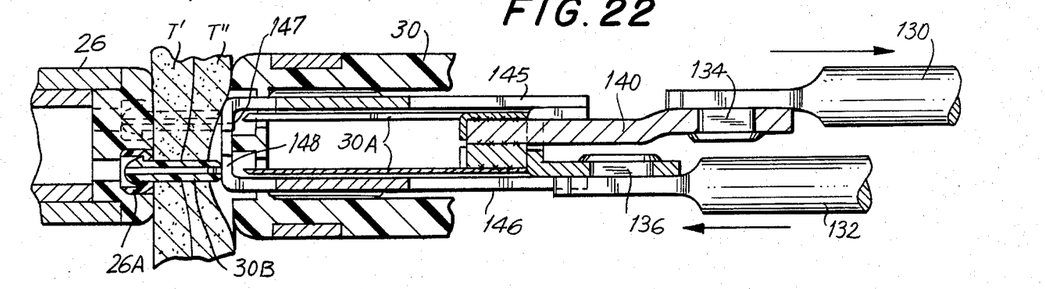

The retainers 26A and their longitudinal extensions 172 and the holes 174 therein and the fasteners 30B and their prongs 162 and the barbs 164 thereon are located in the anvil and fastener-carrying assemblies 26 and 30, respectively, in such a way that each prong 162 of a fastener can be moved distally into a hole 174 in a longitudinal extension 172 of a retainer, with a barb 164 on the prong 162 urging the longitudinal extension 172 of the retainer to expand laterally about the retainer hole 174 until the barb 164 extends distally of the longitudinal extension 172 and the proximal surface 168 of the barb 164 can engage the distal surface 178 of the longitudinal extension 172 about the retainer hole 174 as shown in FIGS. 20 and 22.

Similarly, the piercing members 30A and their distal ends 143A are located in the fastener-carrying assembly 30 so that each piercing member 30A can be moved distally to pierce an opening in tissue, between the anvil and fastener-carrying assemblies 26 and 30, through which opening a fastener prong 162 and its barb 164 can subsequently be moved distally before the prong 162 and barb 164 are moved distally into a retainer hole 174. Preferably, each piercing member 30A is located so that its distal end 143A can also be moved distally into a retainer hole 174 after piercing the tissue.

In the operation of the instrument 10 of this invention as shown in FIGS. 4 to 9, 14, 15 and 19 to 22, two portions of tissue T' and T", to be fastened, are inserted between the instrument's longitudinally spaced, anvil assembly 26 and fastener-carrying assembly 30. The wing nut 16 of the actuating mechanism 32 is then rotated to rotate the threaded rod 106 in the threaded hole 104 of the pusher block 96. This causes the pusher bar 90 and its lateral side members 92 and 94 and block 96 to move distally. Thereby, the bifurcated pusher extensions 100 and 102 on the distal ends of the lateral side pusher members 92 and 94 move the support member 28 distally through the tubular housing portion 14. Distal movement of the support member 28 through the tubular housing portion 14 moves the fastener-carrying assembly 30, on the distal end of the support member 28, distally toward the anvil assembly 26 so that the tissue T' and T" is clamped between the anvil and fastener-carrying assemblies 26 and 30.

Rotation of the wing nut 16 and distal movement of the pusher bar 90 also moves distally the elongated projections 110 and 112 on the lower portions of the lateral side pusher members 92 and 94 and the fourth shaft 122. Thereby, the lower portions 118 of the rectangular frame 38 are also moved distally with the fourth shaft 122. As a result, the rectangular frame 38 and its other two opposite sides 64 and 65 rotate longitudinally about the first shaft 63 from the position of the rectangular frame 38 in FIG. 4 to its position in FIGS. 6 and 8. Such rotation of the rectangular frame 38 moves the distal ends of the pusher rods 34 and 36 from a position beneath the proximal ends of the elongated rods 130 and 132 to a position in which the distal ends of the pusher rods 34 and 36 are adjacent to, and longitudinally aligned with, the proximal ends of the elongated rods 130 and 132, respectively, as shown in FIG. 6. Such rotation of the rectangular frame 38 also serves to move the connecting member 52 into longitudinal alignment with the first pusher rod 34 and first elongated rod 130 and to move the cam follower 54 proximally closer to the first cam surface 80A.

When the rectangular frame 38 is in the position shown in FIG. 4, before rotation of the wing nut 16 and distal movement of the pusher bar 90, the actuating mechanism 32 of the instrument 10 cannot be used to: (a) cause the piercing members 30A to be moved distally to pierce the tissue T' and T" between the anvil and fastener-carrying assemblies or (b) cause the fasteners 30B to be moved distally through holes pierced in the tissue T' and T" and then into holes 174 in the retainers 26A. In this regard, the rectangular frame 38 serves to prevent inadvertent actuation of the instrument 10 until the spacing between the anvil and fastener-carrying assemblies 26 and 30 is such that the tissue T' and T" can be suitably pierced by the piercing members 30A and then fastened with fasteners 30B and retainers 26A.

After rotation of the wing nut 16 and distal movement of the pusher bar 90 to rotate the rectangular frame 38 and to bring the distal ends of the pusher rods 34 and 36 into longitudinal alignment with, and close proximity to, the proximal ends of the elongated rods 130 and 132, the lower portions 21 of the movable second handle 20 can be moved proximally towards the fixed first handle 18, e.g., by squeezing the handles together, to actuate the instrument 10. Proximal movement of the lower portions 21 of the second handle 20 causes longitudinal rotation of the upper portions 66 of the second handle 20 about the second shaft 68. Such rotation of the upper second handle portions 66 causes longitudinal rotation of the segmented drive gear 72 about the second shaft 68. This rotation of the drive gear 72 causes longitudinal rotation of the segmented driven pinion gear 74 about the third shaft 75, which causes longitudinal rotation, about the third shaft 75, of the drive clutch 76 and corresponding rotation of the driven clutch 78 and first cam 80, on which the driven clutch 78 is mounted. Preferably, the first cam 80 is rotated longitudinally a total of approximately 135° by longitudinal rotation of the upper second handle portions 66.

As the lower second handle portions 21 are initially moved proximally, part-way towards the first handle 18, the first cam 80 undergoes a first longitudinal rotation, preferably of approximately 45°. During the first rotation of the first cam 80, the circumferential first cam surface 80A moves progressively closer longitudinally to the retainers 26A and urges the proximal portions of the cam follower 54 to move distally. The distal pressure of the first cam surface 80A against the cam follower 54, during the first rotation of the first cam 80, moves distally the longitudinally aligned, cam follower 54, connecting member 52, first pusher rod 34, first elongated rod 130, and piercing member driver 140 which, in turn, moves distally the two parallel rows 143 of piercing members 30A. The first rotation of the first cam 80 causes the cam follower 54, connecting member 52, first pusher rod 34, first elongated rod 130 and piercing member driver 140 to be moved distally, by the first cam surface 80A, a sufficient distance to that: (a) the distal end 143A of the piercing members 30A and moved distally against, and pierce, the tissue T' and T"; and (b) preferably, the distal ends 143A of the piercing members are then moved further distally into the retainer holes 174. Also during the first rotation of the first cam 80, the second cam 88 on the upper second handle portions 66 rotates with the first cam 80, and the circumferential second cam surface 88A moves progressively closer longitudinally to the retainers 26A but does not contact the proximal end of the second pusher rod 36.

As the lower second handle portions 21 are subsequently moved proximally, the rest of the way towards the first handle 18, the first cam 80 undergoes a second longitudinal rotation, preferably of approximately 45°. During the second rotation of the first cam 80, the second cam 88 undergoes a corresponding second rotation, in which the circumferential second cam surface 88A moves progressively closer longitudinally to the retainers 26A and urges the proximal end of the second pusher rod 36 to move distally. The distal pressure of the second cam surface 88A against the second pusher rod 36, during the second rotation of the first cam 80, moves distally the longitudinally aligned, second elongated rod 132, fastener driver 144, and fastener driver extensions 147 and 148 which, in turn, move distally the two parallel rows of fasteners 26B. The second rotation of the first cam 80 causes the second pusher rod 36, second elongated rod 132, fastener driver 144 and fastener drive extensions 147 and 148 to be moved distally, by the second cam surface 88A, a sufficient distance so that the prongs 162 on the fasteners 30B: (a) are moved distally through the openings, pierced in the tissue T' and T" by the piercing members 30A, and (b) then are moved further distally into the retainer holes 174 to hold the fasteners and retainers together. In this regard, it is preferred that the fasteners 30B be moved distally by the second cam surface 88A, during the second rotation of the first cam 80, so that the fastener prongs 162 extend through the retainer holes 174, distally of the longitudinal extensions 172 of the retainers 26A, with a proximal surface 168 of a barb 164 on each fastener prong 162 engaging a laterally extending, distal surface 178 of a longitudinal extension 172 of a retainer about a retainer hole 174. Thereby, when the first cam 80 has undergone its first and second rotations, the portions of tissue T' and T", between the anvil and fastener carrying assemblies, will have been securely fastened together.

In the operation of the instrument 10, the piercing members 30A initially move distally through the fastener channels 166 to pierce the tissue T' and T". When the fastener prongs 162 subsequently move distally through the openings pierced in the tissue T' and T" and into engagement with the retainers 26A, the fasteners 30B preferably move, at least part way distally, while being supported by the piercing members 30A extending through the fastener channels 166.

Figure 12:
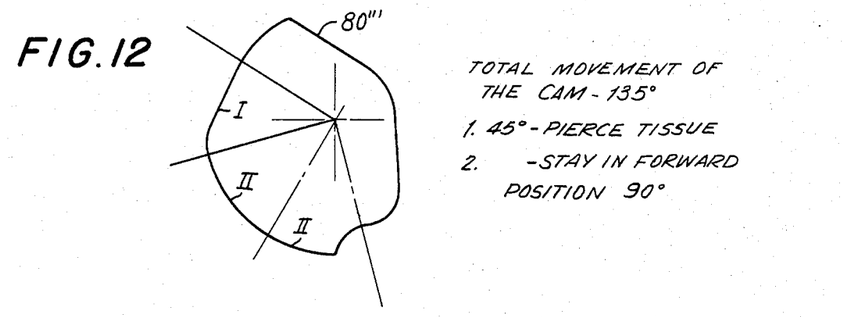
Figure 13:
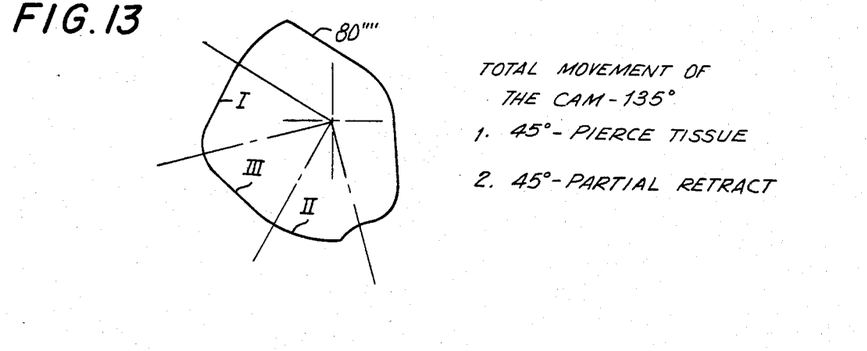

To provide such support for the fasteners 30B, the distal ends 143A of the piercing members 30A can remain distally extended, e.g., in the retainer holes 174, after piercing the tissue T' and T" and while the fastener prongs 162 are moved distally through the tissue and into the retainer holes 174. Thereby, the fasteners 30B would be supported by the piercing members 30A the whole way that the fasteners 30B move distally. For this purpose, one could use, as the first cam 80, the cam 80'" of FIG. 12. As shown in FIG. 12, the first cam surface 80A of cam 80'" would urge the cam follower 54, and thereby the piercing members 30B, to: (a) move distally during the first rotation ("I" in FIG. 12) of the first cam 80'" and (b) remain distally extended during the second rotation ("II" in FIG. 12) of the first cam 80'".

Alternatively, as shown in FIGS. 19 to 22, the distal ends 143A of the piercing members 30A can be retracted, by being moved proximally, after piercing the tissue T' and T" and before the fasteners 30B are moved distally. For this purpose, one could use as the first cam 80: (a) cam 80" of FIG. 11 in order to totally retract the piercing members 30A so that they provide no support to the fasteners 30B during the fasteners' distal movement; or (b) cam 80' of FIG. 10 or cam 80"" of FIG. 13 in order to partially retract the piercing members 30A so that they provide support to the fasteners 30B during part of the fasteners' distal movement. With any of the first cams 80', 80" or 80"", the fifth spring 130A about the first elongated rod 130 shown in FIG. 15: (a) would be longitudinally compressed by the pin 130B, through the first elongated rod 130, when the piercing members 30A are initially moved distally during the first rotation ("I" in FIGS. 10, 11 and 13) of the first cams 80', 80" and 80""; and (b) would subsequently urge the pin 130B and the first elongated rod 130, and thereby the piercing members 30A, to move proximally when the first cam surface 80A no longer urged the cam follower 54 distally during a third rotation ("III" in FIGS. 10, 11 and 13) of the first cams 80', 80" and 80"", following their first rotation and before their second rotation ("II" in FIGS. 10, 11 and 13). Preferably, the third rotation of the first cams 80', 80" and 80"" would be approximately 45°.

Furthermore, the distal ends 143A of the piercing members 30A can, after being moved distally and then being moved proximally, be moved distally again when the fasteners 30B are moved distally in order to provide support to the fasteners during their distal movement. For this purpose, one could use, as the first cam 80, cam 80' of FIG. 10. With first cam 80', the first cam surface 80A would urge the cam follower 54, and thereby the piercing members 30A, to move distally during the second rotation ("II" in FIG. 10) of the first cam 80', following its first and third rotations ("I" and "III", respectively, in FIG. 10).

The terms "longitudinal", "lateral", "distal", "proximal", "lower", "upper", "downward", "upward", "beneath", and the like, as used herein, are relative terms. These terms are used to describe the relative spatial relationships among the various elements of the device for applying surgical fasteners of this invention. The use of such terms, however, should not be construed as limiting the invention in the device.

The term "absorbable" as applied to the fasteners and retainers of this invention is intended to encompass any conventional, plastic-like, biodegradable or human body absorbable material that can be suitably introduced into the human body for fastening body tissue together. Among the suitable absorbable materials for such fasteners and retainers are cat gut (collagen derived from sheep intestinal submucosa), polyglycolic acid, polylactic acid, copolymer blends of polyglycolic acid and polylactic acid, reconstituted collagen, polymers of p-dioxanone, polyesters, polyamino acids such as casein, albumin and the like, polyhydric alcohol polymers such as polyvinyl alcohol, cellulose glycolic acid ethers and esters of alpha-cyanoacrylic acid, such as methyl alpha-cyanoacrylate. Examples of suitable polyglycolic acids are disclosed in U.S. Pat. Nos. 3,463,158, 3,739,773 and 3,772,420. Examples of suitable polylactic acids are disclosed in U.S. Pat. No. 3,636,956. Examples of suitable absorbable polyesters are set forth in U.S. Pat. Nos. 3,225,766 and 3,883,901. Suitable absorbable cellulose glycolic acid ethers are disclosed in U.S. Pat. No. 2,764,159. Examples of suitable esters of alpha-cyanoacrylic acid are found in U.S. Pat. Nos. 3,527,841, 3,564,078 and 3,759,264. Preferably, the absorbable fasteners and retainers of this invention are made from an injection molded, amorphous copolymer of 10-50% (by weight) glycolide and 50-90% lactide. The molecular weight of the copolymer should be from about 30,000-40,000 up to about 130,000.

It will be understood that the embodiments shown and described herein are merely illustrative of the principles of the invention and that various modifications can be made by those skilled in the art without departing from the spirit and scope of the invention, the forms hereinbefore described being merely preferred embodiments. For example, it is contemplated that the housing, wing nut, pusher rods, elongated rods, spacer, fastener prongs, retainer holes, as well as other elements of the instrument and fastening device of this invention, could have lateral cross-sections other than circular, such as square. It is also contemplated that the fasteners, the retainers or both of this invention could be made from other plastic-like materials for fastening devices, besides the absorbable materials. In this regard, it is contemplated that any conventional, flexible and elastic, non-rigid material for fastening devices, such as polyethylene, polypropylene and nylon, could be used as the plastic-like material in the fasteners and/or the retainers of this invention. It is also contemplated that either the retainers or the fasteners of this invention could be made from a non-plastic-like material, such as a metal, e.g., stainless steel. However, it is preferred that the retainers be made of a plastic-like material, and it is particularly preferred that both the retainers and the fasteners be made of a plastic-like material.

We claim:

1. A surgical fastening device for fastening body tissue, which comprises:

a unitary plastic-like retainer having a longitudinal extension; a hole extending longitudinally through the retainer and its longitudinal extension; the retainer being adapted to be positioned on the distal side of the tissue to be fastened; the longitudinal extension of the retainer being laterally expandable about the retainer hole; and a unitary fastener, initially separate from the retainer, having a distally extending prong; the prong being sufficiently rigid to pass through a hole pierced in the tissue to be fastened without additional stiffening means; the fastener being adapted to be positioned on the proximal side of the tissue to be fastened; a laterally extending barb being provided on a lateral surface of the prong; the fastener being adapted to be moved distally so that the prong and its barb: (1) move distally through an opening pierced in the tissue to be fastened, and (2) then move distally into the retainer hole, with the barb urging the longitudinal extension of the retainer to expand laterally, until the barb extends distally of the longitudinal extension of the retainer and a proximal surface of the barb non-releasably engages a laterally extending, distal surface of the longitudinal extension of the retainer about the retainer hole to non-releasably hold the fastener and retainer together and further comprising: a channel extending longitudinally through the fastener and its prong and opening laterally outward from the prong; a pair of barbs on the prong on laterally opposite sides of the fastener channel: the longitudinal center line of the fastener channel; (1) being parallel to the longitudinal center line of the retainer hole and (2) extending within the retainer hole; and the fastener channel being adapted to allow a piercing member and the fastener to move longitudinally with respect to each other, such that: (1) the piercing member can move distally within and with respect to the fastener channel to pierce a hole through the tissue to be fastened, and (2) the fastener and its prong slide distally along the piercing member, such that the prong passes through the hole pierced in the tissue and into the retainer hole to non-releasably hold the fastener and retainer together.

2. The device of claim 1 which comprises:
two parallel prongs on laterally opposite ends of the fastener; and
two parallel longitudinal extensions on laterally opposite ends of the retainer; each longitudinal extension being laterally expandable about a retainer hole.

3. The device of claim 1 or claim 2 wherein each longitudinal extension of the retainer is on the proximal side of the retainer.

4. The device of claim 1 or claim 2 wherein each longitudinal extension of the retainer includes at least one longitudinal slit, communicating with its retainer hole and a lateral surface of the longitudinal extension of the retainer.

5. The device of claim 4 wherein each longitudinal extension of the retainer includes two of the longitudinal slits on opposite sides of the longitudinal extension of the retainer.

6. The device of claim 1 wherein a distal surface of the prong on the fastener is a distal surface of the barb on the prong and the distal end of the fastener channel lies within the distal surface of the barb.

7. The device of claim 1 which further comprises:
two parallel prongs on laterally opposite ends of the fastener; the fastener channels in the prongs extending laterally outward of the prongs in laterally opposite directions; and
two parallel longitudinal extensions on laterally opposite ends of the retainer; each longitudinal extension being laterally expandable about a retainer hole.

8. The device of claim 7 wherein each longitudinal extension of the retainer is on the proximal side of the retainer.

9. The device of claim 1, claim 2, claim 7 or, claim 8 wherein the lateral cross-section of each longitudinal extension of the retainer and each prong of the fastener is annular.

10. The device of claim 1, claim 2, claim 7 or, claim 8 wherein a distal surface of each prong on the fastener is a distal surface of the barb on the prong.

11. The device of claim 10 wherein the lateral cross-section of each longitudinal extension of the retainer, each prong of the fastener and each retainer hole is annular and the longitudinal cross-section of each barb is tapered.

12. The device of claim 1 wherein the fastener is a plastic-like fastener.

* * * * *